United States Patent [19]
Woodmansee et al.

[11] Patent Number: 6,018,999
[45] Date of Patent: Feb. 1, 2000

[54] DIGITAL BOND TESTER

[75] Inventors: Wayne E. Woodmansee, Seattle; Michael J. Duncan, Federal Way; Mark A. Lee, Kent, all of Wash.

[73] Assignee: The Boeing Company, Seattle, Wash.

[21] Appl. No.: 09/138,196

[22] Filed: Aug. 21, 1998

Related U.S. Application Data

[60] Division of application No. 08/958,452, Oct. 27, 1997, Pat. No. 5,831,157, which is a continuation-in-part of application No. 08/715,203, Sep. 18, 1996, abandoned.

[51] Int. Cl.[7] .................................................. G01B 17/02
[52] U.S. Cl. ............................................................ 73/609
[58] Field of Search .............................. 73/602, 609, 610, 73/612, 614, 620, 1.82

[56] References Cited

U.S. PATENT DOCUMENTS

| | | |
|---|---|---|
| 2,903,886 | 9/1959 | Renaut . |
| 4,012,950 | 3/1977 | Kompfner et al. . |
| 4,111,053 | 9/1978 | Geithman et al. . |
| 4,167,879 | 9/1979 | Pedersen . |
| 4,169,385 | 10/1979 | Kellogg et al. . |
| 4,170,144 | 10/1979 | Scott . |
| 4,305,294 | 12/1981 | Vasile et al. . |
| 4,581,937 | 4/1986 | Lang et al. . |
| 5,078,013 | 1/1992 | Kuramochi et al. . |
| 5,303,590 | 4/1994 | Modderman et al. ................... 73/588 |
| 5,309,765 | 5/1994 | Horigome et al. . |
| 5,369,997 | 12/1994 | Roberts et al. ........................ 73/598 |
| 5,417,218 | 5/1995 | Spivey et al. . |

FOREIGN PATENT DOCUMENTS

| | | |
|---|---|---|
| 61-170654 | 8/1986 | Japan . |
| 794-489 | 10/1978 | U.S.S.R. . |
| 1370-548 | 6/1986 | U.S.S.R. . |

*Primary Examiner*—Robert Raevis
*Attorney, Agent, or Firm*—Conrad O. Gardner

[57] ABSTRACT

A digital bond tester operating at frequencies in the kHz range and relying upon vibrational modes which can excite all or substantial portions of the test object.

1 Claim, 9 Drawing Sheets

STARTING FREQUENCY [1-100]: 5
ENDING FREQUENCY [5-33]: 30
NUMBER OF CYCLES [1-10]: 4
SCAN LENGTH [3.0-10.0]: 3.00
VELOCITY [0.1-4.00]: 1.00

MEM. = 53680

| FREQ. | DIFF. | GATE | WAVE |
|---|---|---|---|
| 5 | 39 | 115 | 35 |
| 6 | 43 | 88 | 36 |
| 7 | 58 | 88 | 37 |
| 8 | 66 | 115 | 37 |
| 9 | 77 | 113 | 36 |
| 10 | 118 | 487 | 36 |
| 11 | 170 | 452 | 36 |
| 12 | 187 | 423 | 36 |
| 13 | 202 | 138 | 37 |
| 14 | 243 | 136 | 37 |
| 15 | 304 | 165 | 36 |
| 16 | 371 | 162 | 36 |
| 17 | 466 | 186 | 37 |
| 18 | 585 | 210 | 36 |
| 19 | 737 | 230 | 36 |
| 20 | 881 | 250 | 37 |
| 21 | 991 | 244 | 37 |
| 22 | 934 | 242 | 37 |
| 23 | 851 | 236 | 37 |
| 24 | 775 | 210 | 37 |
| 25 | 677 | 163 | 37 |
| 26 | 627 | 161 | 37 |
| 27 | 543 | 138 | 36 |
| 28 | 498 | 117 | 36 |
| 29 | 500 | 115 | 36 |
| 30 | 488 | 114 | 36 |

DIGITAL BOND TESTER

RELATED APPLICATIONS

This application is a divisional application of continuation-in-part application Ser. No. 08/958,452, filed Oct. 27, 1997, now U.S. Pat. No. 5,831,157, which is a continuation-in-part of application Ser. No. 08/715,203, filed Sep. 18, 1996, now abandoned.

BACKGROUND OF THE INVENTION

The present invention relates to nondestructive testing and more specifically to digital bond testing of composite aircraft structures to sense the presence of manufacturing faults or damage.

Prior art patents utilize some form of ultrasonic probing imaging to detect flaws in parts or members. Several analyze the part at multiple frequencies for maximum return (U.S, Pat. Nos. 5,309,765; 4,170,144; 5,417,218; 4,169,385). Several patents also use a gate to isolate the response at a particular depth or location of the part (U.S. Pat. Nos. 4,167,879; 4,170,144). In contrast, the present invention performs a calibration operation by measuring the maximum difference in the waveform responses between standard (undamaged) and flawed portions of the test article. The gating operation determines the maximum variation between the reference waveform and the test waveform for multiple positions on the part resulting in improved sensitivity.

Query: Is gating a comparison? No, this terminology arises from the manner in which the waveforms are digitized. When a trigger is generated by the motion control electronics of a scanner, the digitizer takes a series of samples of the waveform at the rate of 1 million samples per second. If 500 samples are to be taken, the signal waveform is sampled over a period of 500 microseconds, and these voltage values are used to generate the analog representations of the waveforms. A gate refers to a specific delay after the initiating rigger. Gate 250 would be the time interval 250 microseconds after the trigger signal. Since that delay yielded the largest difference signal between the flaw and reference waveforms at 20 kHz. The sample at that delay would yield the largest response to that type of flaw during a scan.

SUMMARY OF THE INVENTION

It is an object of the present invention to provide an imaging system for evaluating graphite epoxy composite structures.

Aircraft composite skin panels can be damaged due to corrosion, moisture content, or incorrect bonding. Present inspection techniques for evaluating bonds are trial and error using handheld instruments. Hereinafter described is an automated device for nondestructive detection of bonding anomalies or damage to fiberglass and graphite epoxy materials. Acoustic waveforms covering a broad range of frequencies are transmitted into the material and the received waveforms are sampled and stored for several x-y positions on the skin panel under evaluation. The frequency yielding the maximum return is used to image the skin panel. For each position on the test skin panel the corresponding waveform can be gated a different times corresponding to variable material depths maximizing the image resolution. An important feature of the present invention is the broad frequency range (i.e., 5–30 kHz) and gating allowing the instrument to analyze a wide range of materials of varying mechanical stiffness and thickness. Analysis of test samples reveal resolution of anomalies of less than one inch.

DESCRIPTION OF THE PREFERRED EMBODIMENT(S)

Problem Solved

The present digital bond tester incorporates, in a single unit, transmit tone-burst signal generation, digitization, display, and storage of RF receive signals together with generation of C-scan images depicting a part's vibration response. Digital control of the test operation significantly increases the versatility and efficiency of these tests. The digital bond tester enables optimization of the test parameters, generation of multiple C-scan images derived from a single scan, and detection of vibration patterns related to mechanical stiffness of the structure.

Handheld Bond Test Devices

Previous vibration bond testers were developed to perform manual inspections. The operator monitors either a CRT display, meter indications, or audible alarms to detect bonding anomalies or damage. The complex signal changes which occur with these tests are often difficult for an operator to interpret.

Digital Bond Tester

Figure 1:
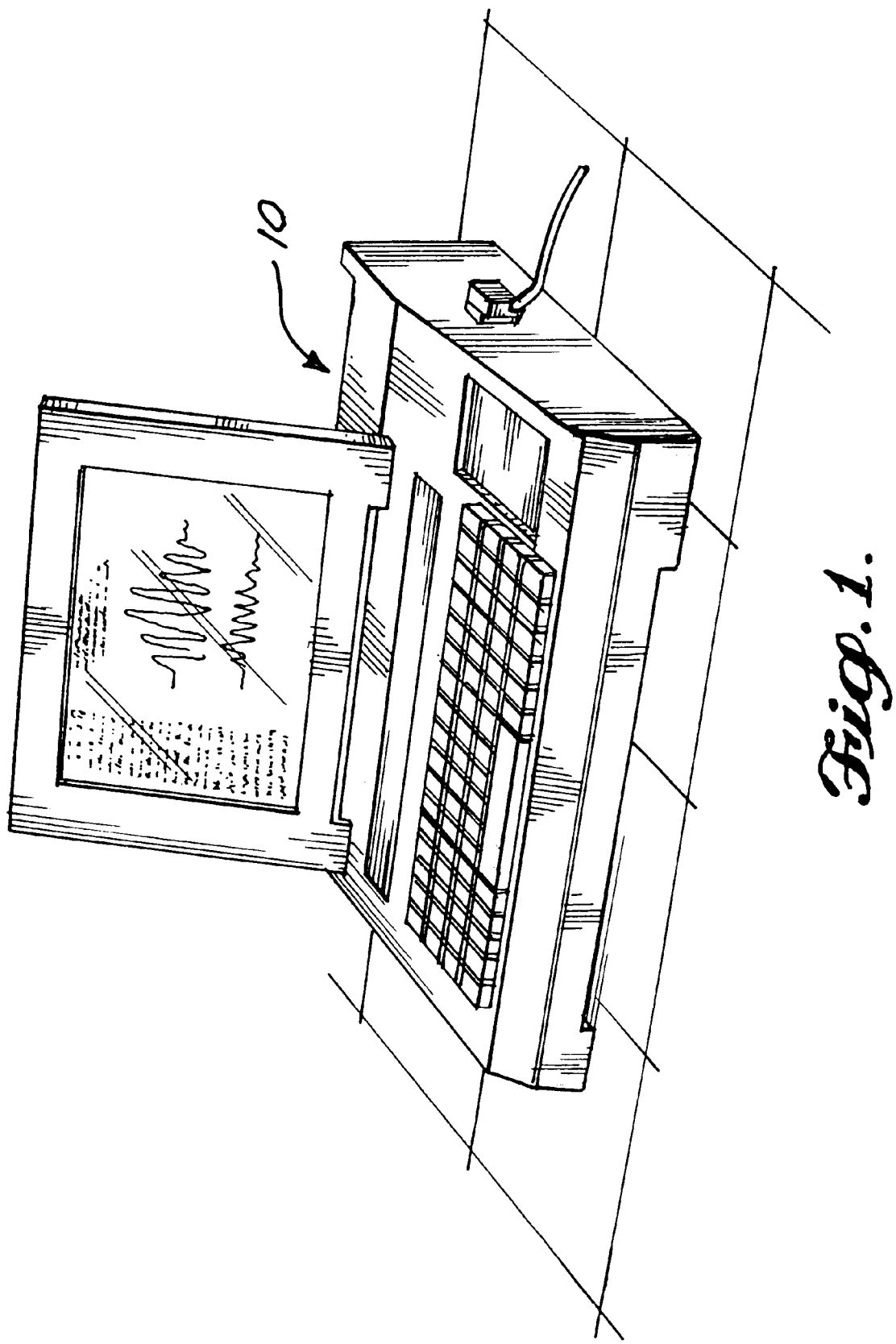
FIG. 1 is a perspective view of a portable PC suitable for displaying waveform and phase displays with C-scan images of raster scanned areas.

The present digital bond tester uses a point-contact, piezoelectric transducer to induce vibrations within a test article and a second transducer detects sound traveling through the part. The two transducers may either by moved together with a fixed separation or one may be stationary and the other moved. The received signals are digitized and displayed on the portable PC of FIG. 1. Two cards within the PC generate and digitize the signals under software control.

The following are either controlled by or enabled by the computer:

Selection of transmit waveform parameters: Tone burst frequency, cycles/burst, and amplitude.

Real time display and storage of 500 point received RF waveforms.

Generation of a real time phase display.

The RF and phase displays are shown both during setup and raster scanning.

Transmit frequency optimization for the structure to be tested.

X, Y motion control, storage of RF waveforms, and generation of real time C-scan image of the test part.

Recall of stored RF waveforms to create selectable C-scan images of signal amplitude or relative phase response.

Measurement of image features and calculation of sound velocity in the test article from interference patterns.

Some of the features of the present digital bond tester are illustrated in the figures in which:

FIG. 1

This is a photo of the portable PC 10 which comprises this instrument. The display is used to present the various waveform and phase displays together with C-scan images.

FIG. 2

In order to select an appropriate test frequency for a given part a display is generated showing the waveforms collected on a "normal" portion of a structure together with the waveform associated with the largest deviation of each frequency tested. Deviation refers to the magnitude of the absolute difference calculated between the reference waveform and each of the waveforms detected over the portion of the part containing a flaw.

Frequency means the series of frequencies between the start and end frequencies that an operator selects. As examples, these could be 4 kHz start and 30 kHz end. All integral frequencies between these values would be tested.

The data can be viewed for each frequency as it is being collected and all of the data can be reexamined upon completion of the test.

Figure 2:
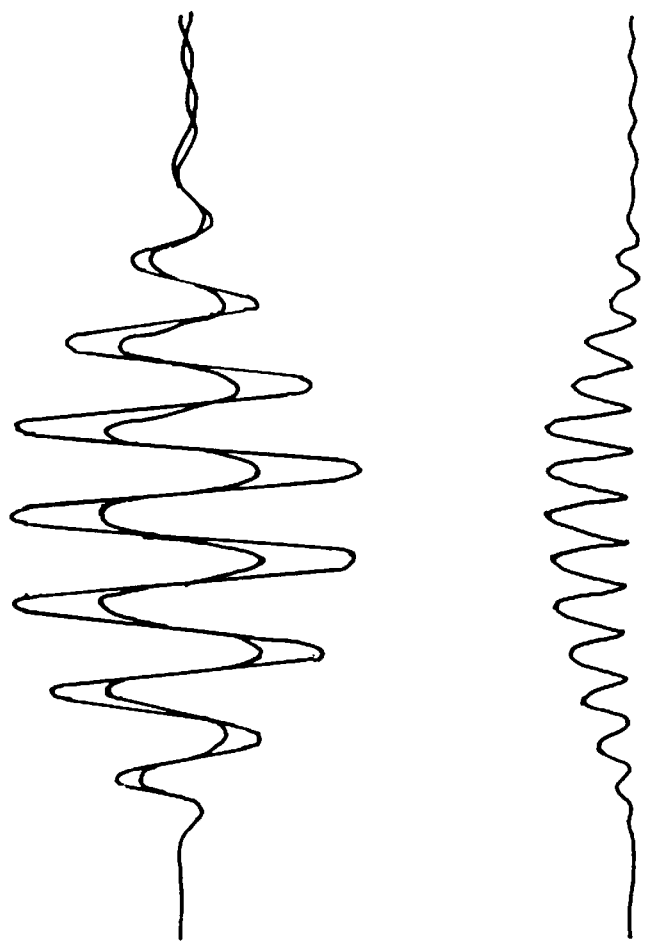
FIG. 2 is a table and waveforms illustrative of a frequency response test on a fiberglass standard panel.

Frequency response test of fiberglass standard panel. Test flaw was on the far side of the 1" thick nomex core. The waveforms shown are for 20 kHz as seen in the columns at the left of the image. The rectangular box that surrounds 20 in the FREQ. Column, 881 in the DIFF column, etc., shows that the waveforms at the right of the figure were collected at that frequency. By pressing the vertical arrow keys on the keyboard, the waveforms for any of the test frequencies can be displayed. In the display on the computer screen corresponding to FIG. 2, the averaged or reference waveform is red while the flaw waveform producing the largest absolute magnitude difference signal at this frequency is shown in white. The waveform at the bottom of the right portion of FIG. 2 shows an analog representation of the magnitude of the difference. RF waveforms are collected at 0.06" intervals for these tests. For a 3" scan this means 16 waves are used to calculate the average or reference wave. The next 32 waves are individually compared with the reference to calculate difference values. The difference value is a number ranging from 1 to 4096 that was measured as the absolute magnitude of the largest difference between the reference waveform and the several waveforms detected over the flaw. In the example shown, the largest absolute magnitude difference at 20 kHz between the reference waveform was detected with waveform 37. Within waveform 37 the largest absolute magnitude difference was measured as 881 at digital sample 250. The line plot at the bottom of the image shows qualitatively the difference between the two waves at each gate point. Gate position is used to specify a specific digitized data sample. In the example in FIG. 2, digital sample 250 (out of 500 which comprise the waveform) produced the largest absolute magnitude difference from the reference waveform.

FIG. 3

Figure 3:
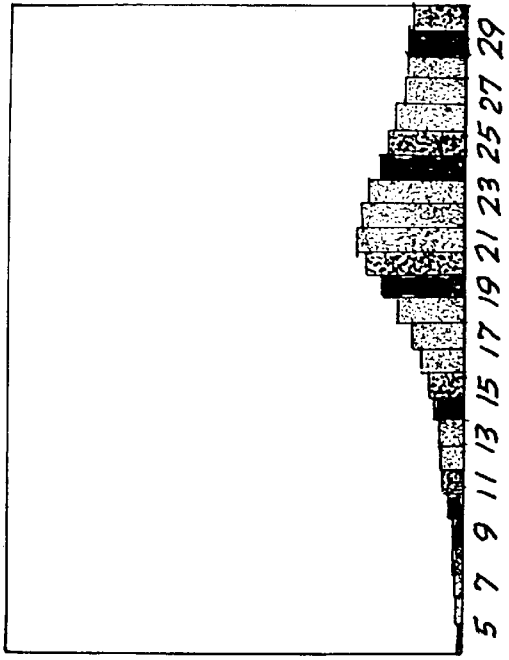
FIG. 3 is a table and histogram illustrative of frequency response results on fiberglass standard.

Based upon the frequency selection test shown in FIG. 3 a histogram is presented showing the maximum difference signal when the reference and test waveforms are compared at each of the 500 sample points comprising the waveforms. Difference is defined as: Absolute magnitude of difference on a sample by sample comparison between waveforms.

Histogram of frequency response results on fiberglass standard. The maximum difference signal (second column at left of image) is plotted versus frequency. The difference signals were for a Teflon insert between the bagside skin and the core. This test was made on the toolside surface.

FIG. 4

Query: How is the operating frequency selected? It is the frequency at which the largest difference values are measured (DIFF column in FIG. 2) for a given flaw. In FIG. 2, 21 kHz gives the largest difference value of 991.

Query: What is the criteria for selection? The selection is the choice of the data sample points to be used for the C-scan image during a scan. From the data in FIG. 2, if 21 kHz was used as the operating frequency, the GATE column shows that data sample 244 would yield the largest difference signal. Setting gate 1 at 244 automatically sets gate 2 at a delay corresponding to a 90 degree phase shift at this frequency relative to gate 1.

The initial gate setting is less critical than the frequency selection since the gate positions can be altered and additional C-scan images can be generated from the stored digital waveforms.

Figure 4:
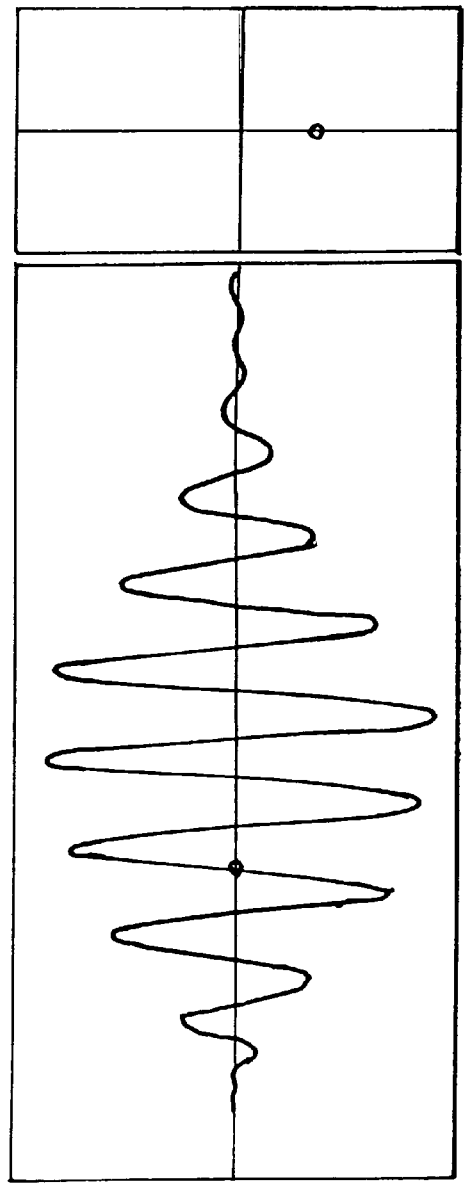
FIG. 4 is illustrative of a waveform detected on fiberglass standard from toolside surface.
Figure 5:
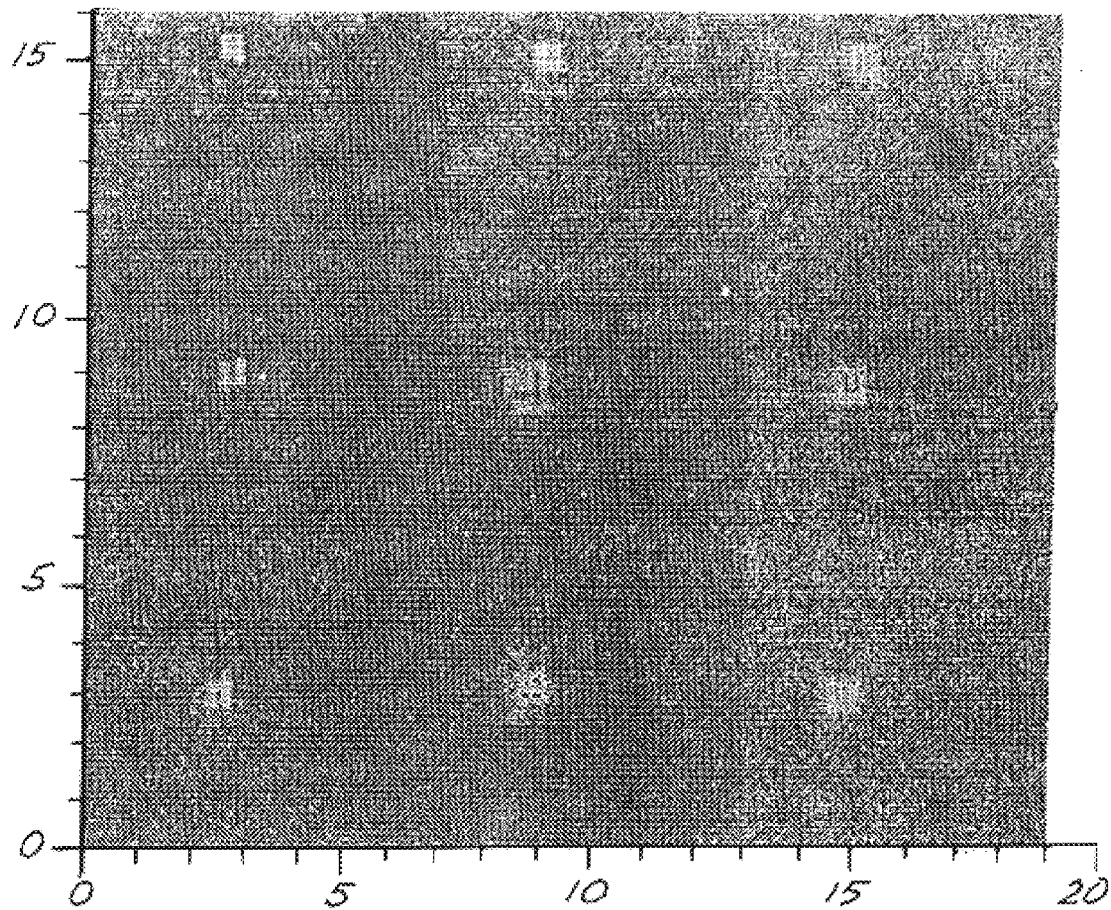
FIG. 5 is an image of a fiberglass skin-nomex core test standard.

After the operating frequency is selected, this display of the waveform is used to select the sample points (gates 1 and 2) that are used to prepare both C-scan images and for the real time phase diagram shown at the right of this figure. During a scan a portion of the received waveform is shown in real time together with the phase display. The small circle at the bottom of the right hand portion of FIG. 4 will rotate as the phase of the detected waveform changes relative to the transmitted signal. The position of the phase display is determined by the data samples selected in the RF waveform at the left of FIG. 4. Gate 1 is at data sample 155 as seen at the third negative peak of the waveform and gate 2 is at the zero crossing at data sample 167. The signal detected at gate 1 yields the vertical position of the phase display spot.

Figure 6:
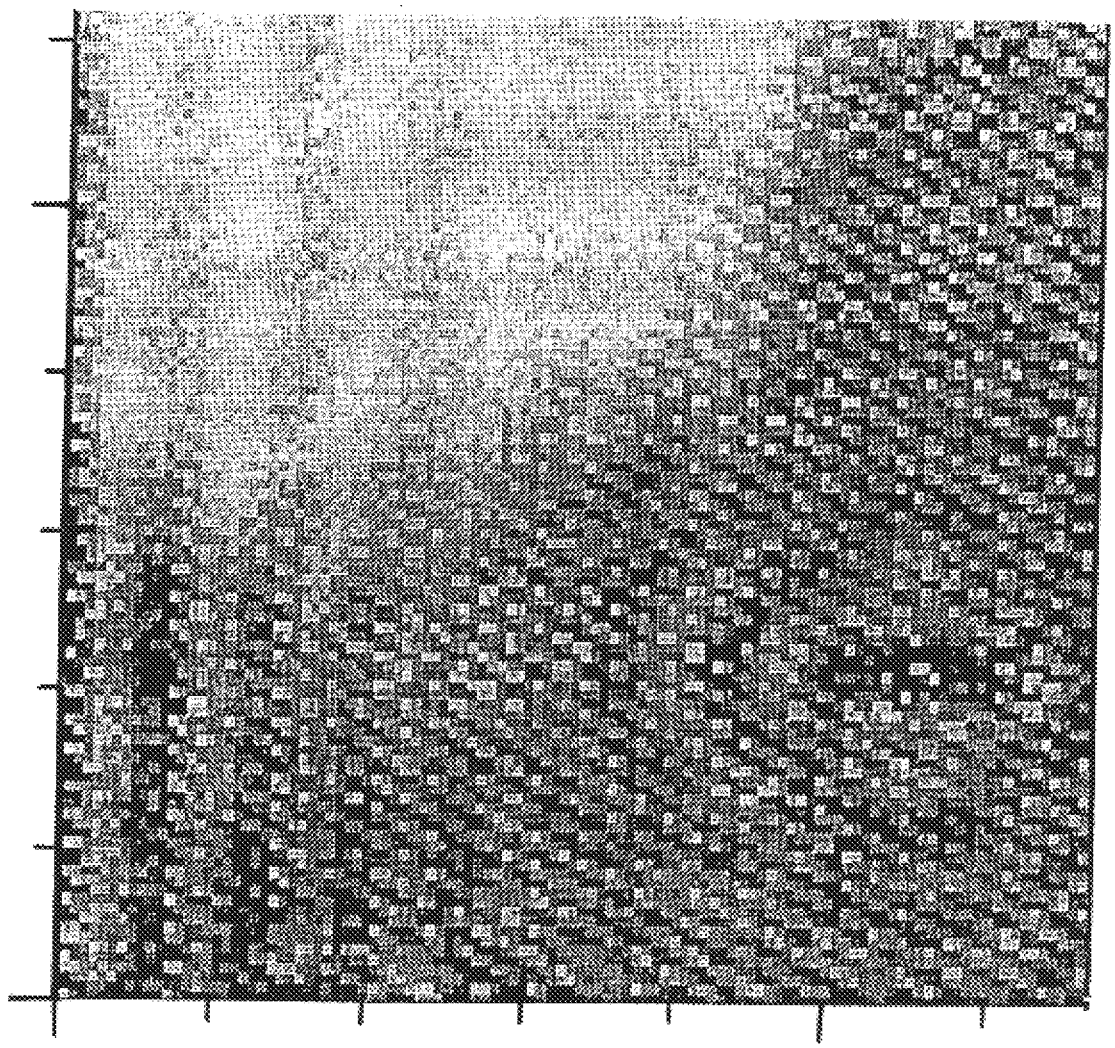
FIG. 6 is an image of an interference pattern at 20 kHz on a fiberglass honeycomb panel.
Figure 7:
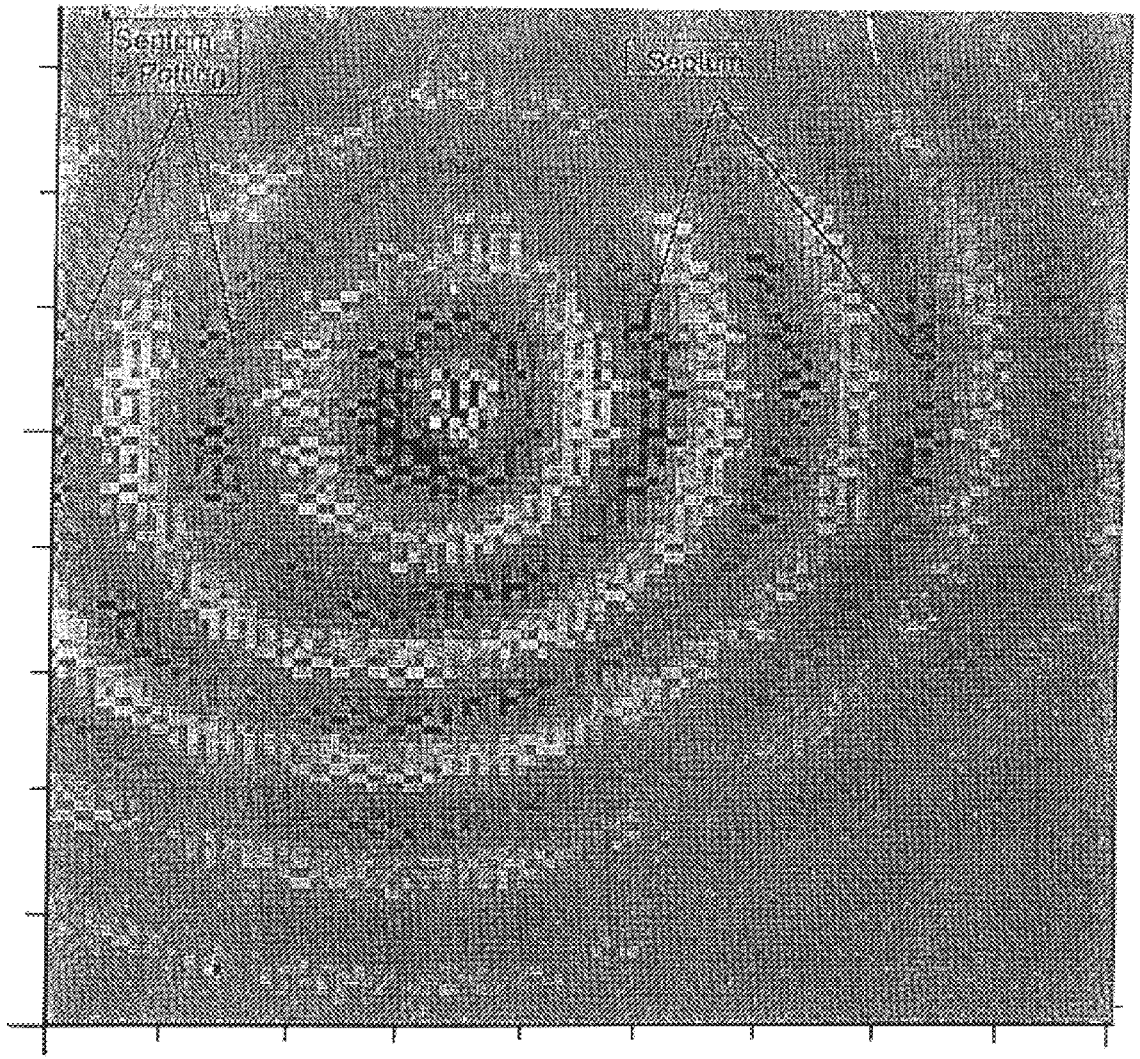
FIG. 7 is an image of fiberglass panel with septum and potting.

Waveform detected on fiberglass standard from toolside surface. Teflon insert was between bagside skin and 1" thick nomex core. These gate settings were used to prepare the image in FIG. 6.

FIG. 5

This is a C-scan image prepared on a fiberglass test standard that represents 9 different skin thickness combinations. This standard is used as a reference for inspecting fiberglass aircraft fairings. Known flaws on both sides of the 1" thick standard were easily seen with this device.

Fiberglass skin-nomex core test standard

Scanned at 20 kHz on toolside surface

Nine different combinations of thickness on toolside and bagside skins

Toolside skin thickness increases from right to left, bagside increases bottom to top Skins are 1, 2 and 3 plies thick Dark indications are inserts beneath the bagside skin White indications are inserts beneath toolside skin

FIG. 6

Interference maxima and minima detected on a septumized fiberglass panel appear as alternating light and dark bands in this image. This effect occurs when signals reflected by an edge or internal discontinuity interfere with signals traveling directly between the two probes. Constructive interference produces locally stronger signals and destructive interference diminishes the local signal. By measuring the spacing of the peaks and valleys the local sound velocity can be calculated. In this sample a 26% increase in sound velocity was measured over an area that contained potting material in one portion of the septumized core. This technique may be useful in assessing damaged areas in composites and in evaluating repairs.

Interference pattern at 20 kHz on fiberglass honeycomb panel. This image was produced on a fiberglass honeycomb panel with an internal septum between two layers of honeycomb. The lighter portion of the image at the upper left is an area with potting material in the core element on the bagside of the panel. This scan was made on the toolside surface. The higher sound velocity over the potted portion of the panel causes the interference pattern at the lower left to broaden as the sound wavelength increases owing to the potting. Individual interference maxima or minima can be traced from the bottom (normal septum construction) to the upper portion of the image (septum+potting material). The elliptical interference pattern at the lower right is generated by an elongated, intentional flaw built into the panel.

FIG. 7

This shows a second means of sensing the local sound velocity. The transmit probe was positioned at the edge of the potted area of the panel shown in FIG. 6. The receive probe was raster scanned over both a septumized portion of the panel and also the region containing potting material. By using fixed phase detection, a series of minima and maxima can be seen which are governed by the sound velocity in the pathway between the stationary and the scanned probes.

Fiberglass panel with septum and potting. Stationary transmitter on bagside surface. Scanned receiver on toolside surface. Fixed phase detection of the signals traveling between the probes result in this phase map which can be used to estimate the local sound velocity. The broadening of the interference peaks on the left is caused by the higher sound velocity in the region of the panel containing potting material. At 25 kHz the wavelengths and sound velocities were estimated to be:

$$\lambda_{Septum} = 1.12'' \quad \lambda_{Septum+Potting} = 1.36''$$

$$C_{Septum} = 28,000 \text{ ips} \quad C_{Septum+Potting} = 34,000 \text{ ips}.$$

Digital Bond Tester Operation
General

The present digital bond tester is a device that measures sound vibration patterns of composite aircraft structures to sense the presence of manufacturing faults or damage. The test probe is comprised of separate transmit and receive piezoelectric transducers mounted side by side in a common body. Small plastic tips couple energy between the spring-loaded transducers and the test surface. One card within portable PC 10 generates a tone burst which is sent to the transmit transducer and a second card digitizes the waveform from the receive transducer. The software stores the digitized data on a disk and selected portions of the waveforms are used to generate images of the data.

There were two fundamental problems with earlier vibration bond test instruments: 1) Selection of an operating frequency that will yield a response to faults in a complex structure has been a trial and error process. 2) The vibration response measured is often quire complex and interpretation of this data is difficult or impossible without a means of scanning an area in a systematic pattern and recording the results. the present digital bond tester addresses these problems through a combination of software and internal electronics to generate and detect vibration signals. The PC controls the transmitted signals as well as the probe motions necessary to perform systematic frequency selection and scanning operations. Four separate C-scan images of the vibration response data are generated from digitized receive waveforms to allow thorough evaluation of both the phase and amplitude behavior of the part being tested. The details of these functions will be discussed in the following.

Figure 8:
FIG. 8 includes the present digital bond tester main menu.

Main Menu (FIG. 8)

This menu is the principal operator interface for conducting tests with the digital bond tester. Query: What is a digital bond tester? Digital bond tester is a name coined since all of the instrument functions are digitally based. The transmitted signals are digitally synthesized tone bursts. Received signals are digitized and stored in computer memory and on various storage media. The frequency selection process is made possible by the calculations which require digital data storage. Multiple C-scan images are calculated from the stored data values. These include amplitude plots from two separate gates, phase plots calculated from the arctangent of the gate outputs, and magnitude plots calculated from the dual plots. The motion control used in both the frequency selection process and X, Y scanning require digital communication with the scan mechanism.

The operations to control the test signal and "gating" of the detected signals are controlled by the F1 function key.

C-scan tests are initiated by the F2 key.

The F3 key starts the frequency selection test.

An image of the display screen is printed on a laser jet printer when the F4 key is pressed.

The F5 key enables viewing and editing of the header of a data file.

The F6 key allows selection and viewing of data files.

A data file that retains only the detected values for two gate positions is saved by the F7 key.

A PCX file to be used for reporting test results is saved with the F8 key.

Four different images (H—horizontal; V—vertical; M—magnitude; and T—arctan) may be selected for display. All of these images are in memory at the same time. Pressing one of these letters causes the corresponding image to be shown.

Pressing A with the mouse cursor on an image feature causes the probe to move to that location on the test part.

C is used to alter the contrast of the displayed image.

When D is pressed distance measurements may be made on the images.

F is used to measure the area of a flaw within an image.

When G is pressed the 500 point waveform stored at the cursor location within the image may be seen. this makes it possible to view the behavior of the detected signal as the cursor moves from normal materials to a flaw.

A linear plot of pixel intensity values is plotted along either a horizontal or vertical line through the image at the location of the cursor when the L key is pressed. Image statistics may be measured along selected lines as well as the signal to noise ratio of image features along the line.

The O key is used to shift alternate display lines left or right to correct offsets in the image owing to scanner backlash.

The color or grayscale palettes used to display the data are selected with the P key.

Statistical measurements may be made within rectangular, circular, or irregular image areas with the S key.

Signals below an adjustable threshold are set to high intensity white with the W key.

The C-scan image is magnified with the Z key as a toggle.

Digital Bond Tester Operational Description

Transmit-Receive Signal Adjustments (F1)

1. The transmit tone burst frequency, peak-peak voltage, and number of cycles is selectable with the F1 key.
2. The Tab key is used to switch between the different parameters (Frequency, Voltage, etc.). Shift Tab reverses the direction in which the parameters are selected. The selected parameter appears blue, and its value can be decreased by means of the < key (above the comma) and increased with the > key (above the period).
3. The RF waveform detected by the receive transducer is shown beneath the parameter display. This waveform is made up from 500 samples of the analog voltage detected by the receive transducer. The two small circles represent sample points on the waveform which are 90° out of phase at the selected frequency. In the accompanying example, the left sample was taken at the 155th voltage value and right was at the 167th value. The delays at which these samples are taken are both adjustable when the Gate 1 parameter is selected. When Gate 2 is selected the delay of the second gate can be adjusted independently of the first gate.
4. The Hor gain and Vert gain are used to expand the display of the horizontal and vertical components of the waveform. They do not alter the data being detected.
5. The Delay display parameter can be used to shift the position of the entire waveform in the window. The smaller display at the right contains a small circle which is used to show relative phase shifts in the detected waveform. The voltage from Gate 1 is the vertical component, and the voltage from Gate 2 provides the horizontal component. Changes in signal amplitude will cause radial movements of he phase circle, and phase changes will result in angular rotations of the circle. These displays are helpful in roughly determining the setup parameters to be used with a test panel and in positioning the probe on the test part prior to the frequency selection test. Manual tests of simple components could also be conducted using these displays.

Test Frequency Selection (The process by which an operating frequency is selected for a given material and flow type)

Introduction

It is important to remember that the waveforms referred to in the following are constructed of a selectable number of sequential digital values that are acquired when a trigger pulse is received from the scan control. The number of samples per waveform can be set to any number up to 1000. To carry out the frequency selection process the test probe is positioned on a "normal" portion of the test material. The probe then undergoes a series of linear scans along a line through the normal material and then across the flaw area. The data acquisition process starts at an operator selected frequency, and the probe is moved along a linear path (typically 3") and then returned to the scan start point, the frequency is incremented, and this process is repeated until the desired range of frequencies has been covered.

The frequency selection process involves the acquisition of several digitized RF waveforms on a "normal" sample of the test material. These are averaged to produce a reference waveform which is stored in memory. This single reference waveform is then compared with each of a series of separate waveforms which are sequentially detected as the probe is moved over a flaw within the part. Both the averaged reference waveform and the separate flaw waveforms are represented by a series of digital values. In the comparison process, the absolute magnitude of the differences between the reference and flaw waveforms is calculated at each data sample. In this way, we determine which of the waveforms generated over the flaw has produced the largest absolute difference from the reference. At the end of this process we have the flaw waveform at each frequency which gave the largest difference as well as the data sample (gate position) within that waveform for which the largest difference was measured. By comparing the data for each frequency tested we know the best frequency for a given flaw as well as the position within the waveform where the largest flaw signal should be detected.

1. Either a standard test part containing intentional flaws or a structure believed to contain a suspect area is used to perform the frequency selection tests. The location of flaws at various depths within a standard should be known in order to position the probe at the proper location for the test.
2. The probe should be mounted in a X,Y scanner and positioned along a line in the X direction centered on the known flaw to be tested. The F1 key should be used to initiate the Transmit-Receive display. Observing this display while moving the probe on and off of the flaw will then aid in positioning the probe for the frequency test. The phase or amplitude displays should show changes when the probe moves from the adjacent, normal material onto the flaw. A typical linear scan for the frequency test is 3 inches. While observing the display, move the probe off the flaw such that it will travel at least 1 inch over normal material and 2 inches over a flaw. Press the Esc key to exit the setup menu.
3. The scanner should provide TTL sample pulses at 0.06" increments in the X direction.
4. Press the F3 key to initiate the frequency selection tests. the start or lowest frequency to be tested should be set. Typically 5 kHz is used.
5. The end or upper frequency should be set. This is dependent upon the probe used, but 30 kHz is a good choice.
6. The number of cycles in the tone burst should be set at 6.
7. The scan length is typically 3.0".
8. The scan velocity commonly used is 2.0 inches/sec.
9. After these values are entered the scanner automatically starts scanning in the X direction. The test frequency is set to the Start value for the first scan line.
10. The first one-third of the scan distance chosen is used to collect RF waveforms from the normal material. For a scan of 3" with sampling at 0.060", 16 waveforms (each with 500 sample points) will be collected from material adjacent to the flaw.
11. The first 16 waveforms are averaged at each sample point to produce a reference or Mean waveform.
12. The next 32 test waveforms collected over the scan line through the flaw are each compared with the reference flaw. The absolute difference between the reference and test waveforms is measured at each of the 500 sample points. The gate or sample position at which this maximum difference is obtained is stored together with the magnitude of the difference. The test waveform is also saved.
13. As the scan continues, the process in item 12 is repeated until the 32nd test waveform has been compared with the reference and each waveform has been saved together with the gate values and maximum difference values for all of the 32 test waveforms.
14. The maximum difference values for the 32 test waveforms are compared, and the test waveform giving the largest difference value is selected. This waveform is then shown on the display together with the mean waveform at this frequency. Beneath the mean and test waveforms is also a display of the maximum absolute difference between the waveforms. The test frequency, maximum difference value, gate location, and the number of the waveform giving the largest difference are listed at the left side of the display.
15. The scanner reverses direction and returns to the scan start location.
16. The frequency in incremented by 1 kHz and a new scan commences along the same 3" path. Steps 10 through 15 are repeated until the end frequency value is reached. The scanner automatically returns to the scan start position after the last frequency scan is completed.
17. The display of frequency test data can then be reviewed by moving the keyboard vertical arrow keys. This moves the frequency selection box along the left columns of data and selects the corresponding waveform and difference plot.
18. This process leads to the frequency, within the range tested, that gives the largest absolute signal for the data evaluated.
19. upon exiting the frequency test, a histogram display is drawn showing the relative difference values at each of the test frequencies evaluated. This also shows the magnitude of the maximum difference value at each frequency and the gate and waveform values that yielded the largest difference.

Date Acquisition
1. Use the F1 key and set the desired frequency, amplitude, number of cycles/tone burst. Set the gate positions, gain and delay settings.
2. The sample pulse electronics should be set to provide trigger signals at the correct scan intervals (e.g., 0.080").
3. Position the probe at the start point for a C-scan.
4. Press the F2 key and provide the header input data including scan length and index width.
5. Input the scan speed.
6. The scan will automatically commence.
7. The type of C-scan image that is drawn during a scan is governed by the last display mode used. If an arctan image was last examined on the display, for example, the new C-scan image will be the same type.
8. Windows in the upper left of the display will show a portion of the RF waveform centered upon the gate positions as well as the phase display. The Tab key can be used to switch between gate settings, gain, and delay to position the viewable portion of the RF waveform. Each time a sample pulse is detected the next 500 point RF waveform will be stored in the computer.
9. From each new waveform the voltages detected at the Gate 1 and Gate 2 locations will be used to update the live C-scan image. The additional three images in memory will be updated at that same time
10. Upon completion of the C-scan the realtime waveform and phase displays will be removed and the main menu functions will be displayed.

Data Analysis
Upon completion of a C-scan test of a questionable area the data can be evaluated both from the initial C-scan images that are available as well as through the stored RF waveforms associated with each image point. The analysis options available are as follows:

1. View each of the four images available. Pressing V yields the image derived from data detected by Gate 1. H switches to the Gate 2 image. The M or magnitude image is developed from the square root of the sum of the squared voltages detected with Gates 1 and 2. The T or arctan image is based upon the arctan of Gate 1/Gate 2. Each of these images represent different aspects of data from the RF waveforms.
2. Different display palettes can be selected for each image by pressing the P key and toggling between different grayscale and color displays.
3. The variability of the data from normal regions can be assessed by measuring the statistics of a region of interest away from any flaw indications. The histogram showing the data distribution from the background or normal area can then be used to set the upper and lower limits for increasing the contrast of questionable image features.
4. When a questionable indication has been found it is often possible to enhance the indication by viewing the RF waveforms as the cursor is moved over the image. When the G key is pressed a display of the waveform corresponding to the cursor location on the image will appear in the upper left corner. As the cursor is moved from portions of the image corresponding to normal material onto a flaw indication, changes in the waveform will be seen. It is often possible to change the gate positions to obtain greater signal changes owing to phase or amplitude changes in the data. The gate locations can be shifted to new locations, and the C-scan image reconstructed by pressing V, H, T or M to generate the Gate 1, Gate 2, Arctan, or Magnitude image. The key that is pressed governs which image is immediately displayed. All of the images will be available after exiting the G menu with the Esc key.

Figure 9:
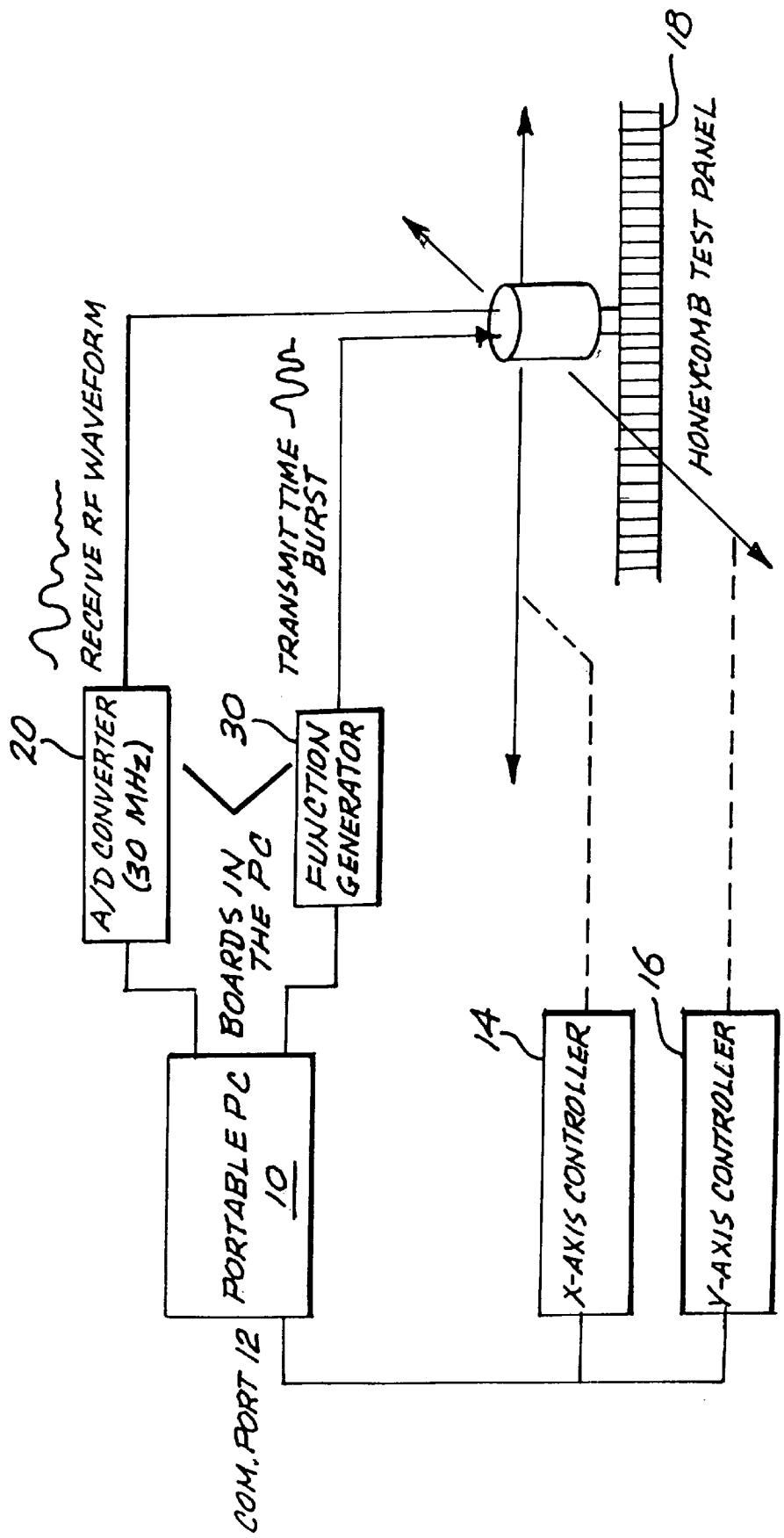
FIG. 9 is a functional block diagram of the present digital bond tester.

DIGITAL BOND TESTER
Functional Diagram (FIG. 9)
Com port 12 of portable PC 10 is coupled to X-axis controller 14 and Y-axis controller 16 for scanning honeycomb test panel 18. 30 MHz AD connector 20 and function generator 30 for receiving the RF waveform and transmitting the tone burst respectively are displayed in portable PC 10.

Features and advantages of the present digital bond tester include the following:

The present system of C-scan images provides four different images of vibrational data. Multiple images derived from separate portions of the detected waveform provide greater insight into the nature and depth of flaws within a structure. The vibrational behavior of typical aerospace structures is too complex to be understood unless it is represented as a two-dimensional image as in the present system.

The present system stores 500 point waveforms at each grid point sampled during a scan thereby rapidly generating multiple images of the same test article. It would otherwise be necessary to rescan the test article for each set of images. The ability to view the RF waveform corresponding to each pixel in the image is a powerful means of enhancing the image of a questionable indication. The visual feedback provided to the operator when the cursor is moved over the image from "normal" to "questionable" indications often allows the gate positions to be changed to more favorable locations along the complex RF waveforms. The C-scan images then generated with the shifted gate positions often improve the contrast of faults that would otherwise be too subtle to detect.

The flexibility to modify data acquisitions and analysis procedures makes the present system a powerful tool for vibrational nondestructive testing.

Other features will become apparent to those skilled in the art upon reading of this specification.

What is claimed is:

1. In combination in a digital bond tester wherein transmitted signals are digitally synthesized tone bursts and received signals are digitized and stored, the method of calculating C-scan images from stored data values comprising the steps of:

providing amplitude plots from two separate gates;

calculating phase plots from the arctangent of the gate outputs; and calculating magnitude plots from the amplitude plots and the phase plots.

* * * * *